(12) United States Patent
van Lune et al.

(10) Patent No.: US 7,951,551 B2
(45) Date of Patent: May 31, 2011

(54) KITS AND REAGENTS FOR LUCIFERASE DETECTION ASSAY SYSTEM

(75) Inventors: Harry van Lune, Aduard (NL); Johan Jochem Bruggeman, Groningen (NL)

(73) Assignee: PerkinElmer Life and Analytical Sciences B.V., Groningen (NL)

( * ) Notice: Subject to any disclaimer, the term of this patent is extended or adjusted under 35 U.S.C. 154(b) by 460 days.

(21) Appl. No.: 12/099,616

(22) Filed: Apr. 8, 2008

(65) Prior Publication Data
US 2009/0053744 A1  Feb. 26, 2009

Related U.S. Application Data

(62) Division of application No. 11/433,791, filed on May 12, 2006, now Pat. No. 7,425,422.

(60) Provisional application No. 60/681,093, filed on May 13, 2005.

(30) Foreign Application Priority Data

May 18, 2005  (EP) ..................................... 05076165

(51) Int. Cl.
C12Q 1/66   (2006.01)
C12M 1/34   (2006.01)
C12M 3/00   (2006.01)
(52) U.S. Cl. ........................... 435/8; 435/287.1; 435/810
(58) Field of Classification Search ........................ None
See application file for complete search history.

Primary Examiner — Robert Landsman
Assistant Examiner — Ian Dang
(74) Attorney, Agent, or Firm — Hoffmann & Baron, LLP

(57) ABSTRACT

The invention relates to methods and kits for detecting enzyme activity using bioluminescence. In particular, it relates to a novel assay system with increased light yield for a sensitive and convenient detection of luciferase activity, such as luciferase reporter enzyme activity. Provided is a method of detecting luciferase activity in a sample, comprising incubating the sample in the presence of luciferin and ATP to allow the generation of a light signal, wherein said light signal is enhanced by performing the incubation in a reaction mixture comprising phosphate and ammonium ions, and measuring the light signal. The invention also relates to kits for use in such method.

22 Claims, 7 Drawing Sheets

KITS AND REAGENTS FOR LUCIFERASE DETECTION ASSAY SYSTEM

The present application is a divisional of application Ser. No. 11/433,791, now U.S. Pat. No. 7,425,422, filed on May 12, 2006, which claims priority from United States Provisional Application bearing Ser. No. 60/681,093 filed 13 May 2005, and European Patent Application bearing Serial No. EP 05076165.9 filed 18 May 2005. The foregoing applications are hereby incorporated by reference herein.

BACKGROUND OF THE INVENTION

The invention relates to methods and kits for detecting enzyme activity using bioluminescence. In particular, it relates to a novel assay system with increased light production for a sensitive and convenient detection of luciferase activity.

Bioluminescence is a naturally occurring phenomenon that has been utilized for a number of applications, particularly in molecular biology where the enzyme associated with it have been used as genetic reporters. Bioluminescence is nearly ideal for use as a genetic marker. Typically there is no endogenous luminescent activity in mammalian cells, while the experimentally introduced bioluminescence is nearly instantaneous, sensitive and quantitative. While numerous species exhibit bioluminescence, only a relative few have been characterized and cloned. Of these, only Firefly (*Photinus pyralis*) luciferase, Renilla luciferase and Aequorin have had much utility. Studies of the molecular components in the mechanism of firefly luciferases producing bioluminescence have shown that the substrate of the enzyme is firefly luciferin, a polyheterocyclic organic acid, D-(−)-2-(6'-hydroxy-2'-benzothiazolyl)-$\Delta^2$-thiazoline-4-carboxylic acid (hereinafter referred to as "luciferin").

Firefly luciferase is a monomeric 61 kD enzyme that catalyses the oxidation of luciferin in a two-step process, which yields light at 560 nm. The first step involves the activation of the carboxylate group of luciferin by acylation with the alpha-phosphate of ATP in the presence of magnesium to produce luciferyl adenylate with the elimination of inorganic pyrophosphate (PPi). In the second step, the luciferyl adenylate is oxidized with molecular oxygen to yield AMP, carbon dioxide and oxyluciferin. The oxyluciferin is generated in an electronically excited state. Upon transition to the ground state the oxyluciferin emits light.

The reaction scheme of the reaction hereinafter referred to a 'luciferin-luciferase reaction' is as follows:

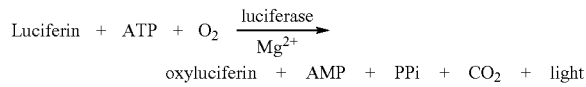

$$\text{Luciferin} + \text{ATP} + O_2 \xrightarrow[\text{Mg}^{2+}]{\text{luciferase}} \text{oxyluciferin} + \text{AMP} + \text{PPi} + CO_2 + \text{light}$$

Luciferase has many characteristics that make it ideal for a reporter enzyme. Its activity is not dependent on any post-translational modification, making it immediately available for quantitation. In addition, the luminescence is very bright, having very high quantum efficiency as compared to many other bio- and chemiluminescent reactions.

When light emission is initiated by the addition of luciferase into a reaction mixture containing ATP, $Mg^{2+}$ (or an other divalent cation such as $Mn^{2+}$), and luciferin, where all components are near or at saturating concentrations, one observes a rapid increase in light intensity followed by a rapid decrease in the first few seconds to a low level of sustained light intensity that may last hours. This rapid decrease in the rate of reaction has been thought to be due to product inhibition. These conventional "flash" type assays using firefly luciferase result in a flash of light, which decays rapidly with the addition of substrates to the enzyme. Especially in automated (e.g. robotic) assay procedures, this is a major problem as it dramatically reduces the time window in which a signal, if present, can be detected. Means for extending the duration of the light signal in the luciferase assay have been eagerly sought.

One approach, which achieved some popularity, to solving the problem of the kinetics of the luciferin-luciferase reaction and the associated difficulty of precisely measuring light emitted during the flash, was to use various inhibitors of the enzyme, which were reported to prevent the flash from occurring or to prolong light production. One such agent is arsenate. Arsenate lowers flash height and tends to prolong the light emission period. The decrease of the intensity of the light signal is considerable undesirable, in particular when microtiter plates or instruments capable of reading out strips are used. In addition, the use of arsenate is not desirable from an environmental point of view.

U.S. Pat. No. 4,246,340 likewise proposes a method for prolonging the light signal in a luciferin-luciferase assay based on the use of inhibitors, such as analogs of D-luciferin. This prolongs the light signal from seconds to a few minutes.

The cofactor coenzyme A (CoA) has been reported to affect the pattern of light emission in the luciferin-luciferase reaction. Airth et al., Biochimica et Biophysica Acta, vol. 27 (1958) pp. 519-532, report that, when CoA is added to a firefly luciferin-firefly luciferase reaction mixture, there is no effect on the initial peak of light intensity but luminescence will continue at a higher level for a time period that is proportional to the total CoA added. Airth et al. have shown that the total light emitted is greater in the presence of CoA than in its absence. U.S. Pat. No. 5,283,179 also discloses the addition of coenzyme A (CoA) in the assay reagent to yield greater enzyme turnover and thus greater luminescence intensity. This resulted in an increased light output that is maintained for at least 60 seconds.

It has been reported that other sulfhydryl compounds contribute to the stability of luciferases during preparation and storage of the enzymes. U.S. Pat. No. 4,833,075 discloses that dithiothreitol (DTT) will maintain luciferase activity at a level of 50% in an aged *Photinus pyralis* luciferase solution which, without the DTT, would have only 10% residual enzymatic activity compared to a freshly prepared luciferase solution. U.S. Pat. No. 4,614,712 describes that, when bacterial luciferase has been inactivated by disulfide formation, enzyme activity may be restored by addition of DTT, β-mercaptoethanol (β-ME), or other reducing agents.

U.S. Pat. No. 5,618,682 describes compositions and methods for increasing the duration of detectable photon emission of a luciferin-luciferase reaction. To that end, the reaction mixture containing luciferase, luciferin, ATP, and cofactors required for luciferase catalytic activity is mixed with a composition containing adenosine monophosphate, a radical scavenger (DTT) and a chelating agent (EDTA).

U.S. Pat. No. 5,650,289 reports that the combined use of CoA and DTT in the reaction mixture positively influences the kinetics of the luciferin-luciferase reaction. The half-life of the light signal, i.e. the time period after which 50% of the original light signal is observed, was assessed at 300 to 500 seconds.

It is an object of the present invention to provide an alternative luciferase detection assay system with improved light yield and extended-glow light emission for sensitive detection of firefly luciferase reporter enzyme.

SUMMARY OF THE INVENTION

Surprisingly, it has been found that this goal is met by performing the luciferin-luciferase reaction in the presence of phosphate anions and ammonium cations. The invention therefore relates to a method for detecting luciferase activity in a sample, comprising incubating the sample, or a part thereof, in the presence of luciferin and ATP and any required cofactor (e.g. $Mg^{2+}$ or $Mn^{2+}$) to allow the generation of a light signal, wherein said incubation is performed in a reaction mixture comprising phosphate and ammonium ions to enhance said light signal, and measuring the light signal.

As is shown herein, the combined presence of ammonium and phosphate in the reaction mixture yields a strong light signal which is stable for a relatively long period of time. A half-life of the light signal ranging from 30 minutes up to 8 hours can be achieved.

An advantage of the present invention is that it provides improvements in the kinetics of light production and the total light produced in the luciferin-luciferase reaction which render assaying for luciferase simple and sensitive. For example, with the methods or test kits of the present invention, the assays do not require special procedures, such as rapid sample injection, or special equipment, such as sophisticated luminometers, to measure the light emitted in the rapid flash of conventional luciferin-luciferase reactions. Indeed, using the methods and compositions or kits of the present invention, it is possible that devices, such as scintillation counters, that are already available in most laboratories for other types of measurements, can be employed in assays requiring measurement of light produced in a luciferin-luciferase reaction. This significantly expands application of such assays in science and technology by facilitating use of the assays in laboratories that do not have luminometers but do have scintillation counters or other devices for measuring light production.

Another advantage of the methods or test kits of the present invention is that due to the sustained high signal a large number of samples can be prepared in microplates and assayed for luciferase activity. This is especially useful in both batch wise and continuous processing of the samples in High Throughput Screening (HTS) applications.

DETAILED DESCRIPTION OF THE INVENTION

According to the invention, the reaction mixture contains relatively high concentrations of both phosphate and ammonium ions. Generally speaking, it is observed that the higher the phosphate concentration the higher the total light yield of the luciferin-luciferase reaction. The total light yield or total luminescence refers to the area under the curve representing the detectable light units as a function of time. It is determined by the peak intensity (i.e. the initial light burst upon combining enzyme and substrates) and the rate at which the intensity decreases after the peak intensity is achieved.

The total phosphate concentration in the reaction mixture is preferably at least 10 mM, preferably at least 25 mM, more preferably at least 60 mM, most preferably at least 100 mM. For example, a phosphate concentration of 125 mM, 150 mM, 200 mM, 500 mM or 1 M can be used. As exemplified in the Examples below, phosphate concentrations up to 1.4 M phosphate were tested, which yielded good results in terms of the initial light signal and the duration of the light signal. The term "phosphate" as used herein refers a polyatomic ion or radical consisting of one phosphorus atom and four oxygen. In the ionic form, it carries a −3 formal charge, and is denoted $PO_4^{3-}$. In a biochemical setting, a free phosphate ion in solution is called inorganic phosphate. Inorganic phosphate is generally denoted $P_i$. Suitable sources of phosphate include phosphoric acid ($H_3PO_4$) and its salts, such as alkali salts or earth alkali salts of $PO_4^{3-}$, $HPO_4^{2-}$ and $H_2PO_4^{-}$.

The term "ammonium ion" as used herein refers to a cation of the general formula $NR_4^+$, wherein R can essentially be any group. Preferred R groups include aliphatic groups like linear or branched hydrocarbons, optionally substituted e.g. by a hydroxyl, and hydrogens. The four R groups which coordinate the nitrogen atom can be the same or different. Ammonium ions can be supplied to the reaction mixture by any compound capable of providing a $NR_4^+$ ion in an aqueous solution. In one embodiment, ammonium ions are provided by one or more ammonium ($NH_4^+$) salts, such as $(NH_4)_2SO_4$, $NH_4H_2PO_4$ and $(NH_4)_2HPO_4$. $NH_4H_2PO_4$ and $(NH_4)_2HPO_4$ are very suitable since these salts provide both phosphate anions as well as ammonium cations. In a further embodiment, ammonium ions can be provided by protonated amines. An amine is an organic derivative of ammonia ($NH_3$). One, two or three alkyl groups may replace the hydrogens of ammonia to give primary, secondary or tertiary amines, respectively. Like ammonia, the ammonia derivatives, the amines, are weak bases. This means that aqueous solutions of amines are alkaline if one mixes an amine with water, the lone pair on nitrogen can abstract a proton from water generating an ammonium ion and a hydroxide ion.

According to the present invention, a final concentration of 1 M ethanolamine is assumed to provide the aqueous reaction mixture with 1M of ammonium ions. Thus, the concentration of ammonium ions in the reaction mixture is regarded to be identical to the concentration of the compound (buffer, salt etc.) source of ammonium ions in the reaction mixture.

Regular aliphatic amines have about the same base strength, with pKb's in the range of 3-4, and are slightly stronger bases than ammonia. The increase in basicity compared with ammonia can be attributed to the greater stability of an alkylammonium ion, as for example, $RCH_2NH_3^+$, compared with the ammonium ion, $NH_4^+$. This greater stability arises from the electron-donating effect of alkyl groups and the resulting partial delocalization of the positive charge from nitrogen onto carbon in the alkylammonium ion. Aromatic amines are much weaker bases, with pKb's around 9-13. This can be explained by resonance delocalisation of the lone pair electrons into the aromatic π-system.

As is clear from the above, the present invention discloses that the combined presence of phosphate and ammonium ions in the luciferin-luciferase reaction mixture enhances the total luminescence of a luciferase detection system. It is to be noted (see e.g. Example 4 herein below) that this beneficial effect on total light yield is not observed in a system for ATP detection which, as in a luciferase detection system, also employs the luciferin-luciferase reaction. In an ATP assay the large amount of luciferase (as assay reagent) and the low amount of ATP (present in the sample) in combination with large quantities of Tris-phosphate ions, give rise to a lower total luminescence than with no or lower quantities of Tris-phosphate present in the assay mixture. In contrast, increasing the amount of Tris-phosphate ion concentrations enhanced the light output of the luminescence reaction in a luciferase detection assay mixture, comprising large quantities of ATP (being an assay reagent) and a low amount of luciferase (from the sample). It has been reported that the enzyme characteristics of firefly luciferase differ between assays set up for ATP- and luciferase detection, respectively. See for example Ye et al. in "A Practical Guide to Industrial Uses of ATP-Luminescence in Rapid Microbiology" published in 1997 by Cara Technology Limited, Lingfield). The distinct effects of the combination of ammonium and phosphate ions on the luciferase-detection system and the ATP-detection system as disclosed in the present invention are very likely related to the different enzyme characteristics. In one embodiment, a method of the invention comprises detecting luciferase activity in a sample, comprising incubating the sample in the presence of luciferin and an excess (relative to luciferase) of ATP and a bivalent cation to allow the generation of a light signal, wherein the total light yield of said light signal is enhanced by performing the incubation in a reaction mixture comprising ammonium ions and at least 20 mM phosphate ions and ammonium ions, and measuring the light signal. Preferably, the concentration of ATP in the luciferin/luciferase assay mixture is at least 0.05 mM, preferably at least 0.1 mM, for example in the range of 0.5-5 mM ATP.

In a method of the invention, the amine used is preferably protonated at the pH of the reaction mixture, which typically ranges between pH 5 and 9. This means that the pKb of the amine is preferably below the desired pH of the reaction mixture. Table 1 below lists some examples of amines and their pKb values. Primary and secondary alkyl- or alkanolamines, such as ethylamine, diethylamine, ethanolamine and diethanolamine, appear particularly useful in a method of the invention. However, certain tertiary amines like triethylamine can also be used.

Amine-based buffers are particularly useful in practicing the present invention. Examples of amine-based buffers include Tris (tris(hydroxymethyl)aminomethane and Bis-Tris(bis(2-hydroxyethyl)imino]-tris(hydroxymethyl)methane). Furthermore, heterocyclic amines may be used. In a heterocyclic amine, a five- or six-atom ring contains one or more nitrogen atoms. An example is imidazole.

TABLE 1

The structure, pKb and pKa of various amines

| Amine | Structure | pkb | pKa |
|---|---|---|---|
| Ammonia | NH$_3$ | 4.74 | 9.26 |
| Primary Amines | | | |
| methylamine | CH$_3$NH$_2$ | 3.36 | 10.64 |
| ethylamine | CH$_3$CH$_2$NH$_2$ | 3.19 | 10.81 |
| isopropylamine | (CH$_3$)$_2$CHNH$_2$ | 3.18 | 10.82 |
| tert-butylamine | (CH$_3$)$_3$CNH$_3$ | 3.17 | 10.83 |
| cycloheylamine | C$_6$H$_{11}$NH$_2$ | 3.34 | 10.66 |
| Secondary Amines | | | |
| dimethylamine | (CH$_3$)$_2$NH | 3.27 | 10.73 |
| diethylamine | (CH$_3$CH$_2$)$_2$NH | 3.02 | 10.98 |
| piperidine | 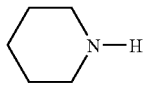 | 3.25 | 10.75 |
| Tertiary Amines | | | |
| trimethylamine | (CH$_3$)$_3$N | 4.19 | 9.81 |
| triethylamine | (CH$_3$CH$_2$)$_3$N | 3.25 | 10.75 |
| Aromatic Amines | | | |
| aniline | 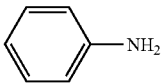 | 9.37 | 4.63 |

TABLE 1-continued

The structure, pKb and pKa of various amines

| Amine | Structure | pkb | pKa |
|---|---|---|---|
| 4-methylaninline | 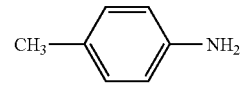 | 8.92 | 5.08 |
| 4-chloroaniline | 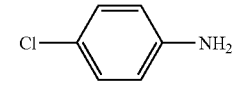 | 9.85 | 4.15 |
| 4-nitroaniline | 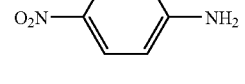 | 13.0 | 1.0 |
| Heterocyclic Aromatic Amines | | | |
| pyridine | 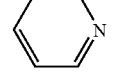 | 7.75 | 5.25 |
| imidazole | 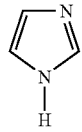 | 7.05 | 6.95 |

Still further, zwitterionic compounds can be used to provide the luciferase reaction mixture with ammonium ions. By definition, a zwitterion (from the German "zwei", meaning "two") is an ion that contains both positively and negatively charged ions in the same molecule. A zwitterion can be formed by compounds which contain both, acidic and basic groups. Amino acids are typical examples of zwitterionic compounds. Since both carboxyl and amino functions are present in amino acids, these two functional groups tend to react with each other in the same way, yielding an "internal salt", which contains both the carboxylate anion and an ammonium cation function. The equilibrium lies far to the salt, so the predominant structure of an amino acid is the zwitterionic structure. For example, glycine contains both a basic amino group (NH$_2$) and an acidic carboxyl group (COOH); when these are both ionized in aqueous solution, the acid group loses a proton to the amino group, and the molecule is positively charged at one end and negatively charged at the other. In a substantially acidic solution, the carboxylic acid function of the zwitterion is protonated, thus forming a cationic structure which has an ammonium ion functional group. This is the conjugate acid of the zwitterion (and also of the neutral, uncharged, form of the amino acid, by protonating the amino group). According to the invention, zwitterionic compounds having a pKa of the conjugated acid of the amino group above the pH of the luciferine-luciferase reaction mixture are preferred, as this ensures that the amine moiety is protonated.

Another class of useful zwitterionic compounds is represented by the zwitterionic buffers. Table 2 lists some exemplary common zwitterionic buffers which may be used in the present invention. The invention is however not limited to the use of those zwitterionic buffers listed below.

TABLE 2

Zwitterionic Buffers

| Buffer | Structure and Name | MW | pKa at 20° C. (D/° C.) | useful pH range |
|---|---|---|---|---|
| ACES | $H_2NCCH_2NH(CH_2)_2SO_3H$ (with C=O) <br> N-(2-acetamido)-2-aminoethanesufonic acid | 182.2 | 6.88 (−0.020) | 6.4-7.4 |
| ADA | $H_2NCCH_2N(CH_2CO_2H)_2$ (with C=O) <br> N-(2-acetamido)iminodiacetic acid | 190.2 | 6.62 (−0.011) | 6.4-7.4 |
| BES | $HO_3SCH_2CH_2N(CH_2CO_2H)_2$ <br> N,N-bis(2-hydroxyethyl)-2-aminoethanesulfonic acid | 213.3 | 7.17 (−0.016) | 6.6-7.6 |
| Bicine | $HO_2CCH_2N(CH_2CO_2H)_2$ <br> N,N-bis(2-hydroxyethyl)glycine | 163.2 | 8.35 (−0.018) | 7.8-8.8 |
| CAPS | $C_6H_{11}NH(CH_2)_3SO_3H$ <br> 3-(cyclohexylamino)-1-propanesulfonic acid | 221.3 | 10.4 (0.032) | 9.7-11.1 |
| CHES | $C_6H_{11}NH(CH_2)_2SO_3H$ <br> 2-(cyclohexylamino)-1-ethanesulfonic acid | 207.1 | 9.55 (−0.011) | 9.0-10.1 |
| HEPES | $HOH_2CH_2C-N\underset{\frown}{\frown}N-(CH_2)_2SO_3H$ <br> 4-(2-hydroxyethyl)piperazine-1-ethanesulfonic acid | 238.3 | 7.55 (−0.014) | 7.0-8.0 |
| HEPPS (EPPS) | $HOH_2CH_2C-N\underset{\frown}{\frown}N-(CH_2)_3SO_3H$ <br> 4-(2-hydroxyethyl)piperazine-1-propanesulfonic acid | 252.3 | 8.0 (−0.011) | 7.6-8.6 |
| MES | (morpholine)$N-(CH_2)_2SO_3H$ <br> 2-morpholinoethanesulfonic acid monohydrate | 213.3 | 6.15 (−0.011) | 5.8-6.5 |
| MOPS | (morpholine)$N-(CH_2)_3SO_3H$ <br> 3-morpholinopropanesulfonic acid | 209.3 | 7.2 (−0.011) | 6.5-7.9 |
| PIPES | $HO_3S(H_2C)_2-N\underset{\frown}{\frown}N-(CH_2)_2SO_3H$ <br> piperazine-1,4-bis(2-ethanesulfonic acid) | 302.4 | 6.82 (−0.009) | 6.4-7.2 |
| TAPS | $(HOH_2C)_3CNH(CH_2)_3SO_3H$ <br> N-[tris(hydroxymethyl)methyl]-3-aminopropanesulfonic acid | 243.3 | 8.4 (0.018) | 7.7-9.1 |
| TES | $(HOH_2C)_3CNH(CH_2)_2SO_3H$ <br> N-[tris(hydroxymethyl)methyl]-2-aminopropanesulfonic acid | 229.3 | 7.5 (−0.020) | 7.0-8.0 |
| Tricine | $(HOH_2C)_3CNHCH_2CO_2H$ <br> N-[tris(hydroxymethyl)methyl]-glycine | 179.2 | 8.15 (−0.021) | 7.6-8.8 |

In a method of the invention, the reaction mixture pH typically ranges between 5 and 9, preferably between 6.5 and 8.2.

As will be clear from the above, many combinations of phosphate sources and ammonium sources can be used in a luciferase reaction mixture of the invention. More than one source for a given ion may also be used. Certain combinations of phosphate/ammonium sources were found to be particularly useful. Of specific interest for use in the present invention is the combination of an amine-based ionic buffer, like Tris or Bis-Tris, which is neutralized with phosphoric acid.

The concentration of ammonium ions in the luciferase reaction mixture of the invention can vary. A concentration of at least 20 mM, better more than 60 mM ammonium ions is preferred. Very good light yields can be observed at a concentration of more than 100 mM ammonium ions, even better at more than 200 mM ammonium ions, for example 250 mM Tris or ethanolamine or 500 mM ammonium ($NH_4^+$).

According to the invention, the concentration of phosphate ions and ammonium ions in the reaction mixture can be the same or they can be different. In one embodiment, the concentration of ammonium ions is higher than the concentration of phosphate ions. In another embodiment, the concentration of ammonium ions is lower than the concentration of phosphate ions. In a specific aspect, ammonium ions are present in excess of the phosphate ions, for example at least a 1.1-fold excess, preferably at least 1.4-fold excess, such as 1.5, 1.7, 1.8 or even 2-fold excess of ammonium ions. As exemplified below, very good results can be obtained using Tris as source of ammonium ions in excess (e.g. 2-fold) of phosphoric acid (as source of phosphate ions), in particular with a phosphate concentration of at least 60 mM and/or with an ammonium ion concentration of at least 120 mM (see Table 3). See Tables 4 and 5 which demonstrate the effect of increasing concentrations ethanolamine (Table 4) or ammonium (Table 5) and phosphate on the total light yield of the luciferase reaction. Also here, ammonium ions are present in excess of phosphate ions. This is the result of neutralizing the solution containing the ammonium ions (Tris, ethanolamine, ammoniumphosphate) with phosphoric acid to pH 7.0. Of course, it is not a prerequisite that the final pH of the aqueous reaction mix is controlled solely by the ammonium and phosphate ions. For example, the invention also encompasses a reaction mixture comprising phosphate ions in excess of ammonium ions which is neutralized by an alkaline agent which is not a source of ammonium ions, like NaOH, KOH and the like. In a similar fashion, acidic agents other than those contributing phosphate ions can be used to set the pH at a desired value.

In one embodiment, the combination of Tris buffer and phosphoric acid is used. For example, a two-fold detection buffer comprising 125 mM Tris neutralized with 63 mM $H_3PO_4$ provides sufficient phosphate and ammonium ions to the reaction mixture to positively affect the magnitude and kinetics of the light signal. Increasing the Tris and/or phosphate concentration further enhances this effect (see also FIG. 1). Very satisfactorily results were obtained in a reaction mixture comprising at least 250 mM Tris, accompanied with at least 125 mM phosphate.

Other useful combinations include mono- and di-alkanolamines and phosphoric acid. In one aspect, the luciferase reaction mixture comprises ethanolamine neutralized with phosphoric acid to approximately pH=7.0 (see FIG. 2).

The reaction mixture preferably also comprises a stabilizer for luciferase. Suitable examples of stabilizers are mammalian serum albumin, a lactalbumin and an ovalbumin. The use of bovine serum albumin (BSA) is preferred. The amount of stabilizer will typically be below 1 wt %, calculated based on the total weight of the reaction mixture. Further, the reaction mixture preferably comprises a sequestering agent like ethylenediaminetetraacetic acid (EDTA), ethylene glycol-bis(2-aminoethylether)-tetraacetic acid (EGTA) or cyclohexane-1, 2-diaminetetraacetic acid (CDTA). The sequestering agent is generally present in an amount of 0.1 to 25 mM.

Methods for detecting luciferase activity known in the art typically comprise thiol-containing compounds, such as DTT and/or CoA (see for example U.S. Pat. No. 5,650,289). Whereas thiols reportedly contribute to the stability of luciferase and improve the kinetics of light production, they have several drawbacks. Formulations containing thiols have a pungent odour. Furthermore, thiols experience auto-oxidation in solution and, as a consequence, are not stable for long times. The present inventors unexpectedly observed that thiol-compounds in a luciferase reaction mixture are no longer necessary if both ammonium and phosphate ions are present. It was found that the overall light production in the absence of thiols but in the presence of ammonium ions (e.g. provided by a Tris buffer) and phosphate ions was similar to or even surpassed the light production in the presence of thiols. Herewith, the invention provides a method of detecting luciferase activity in a sample, comprising incubating the sample in the presence of luciferin, ATP and a divalent cation (e.g. $Mg^{2+}$ or $Mn^{2+}$) to allow the generation of a light signal, wherein said incubation is performed in a reaction mixture comprising phosphate and ammonium ions in the relative absence of a thiol-containing compound, and measuring the light signal. The expression "in the relative absence of a thiol-containing compound" is meant to indicate that no exogenous or supplementary thiol compound, such as DTT, glutathione and/or CoA, is added to the reaction mixture. In one embodiment, the reaction mixture and assay reagent of the invention is free or essentially free of thiol-compounds. It may however occur that a sample to be assayed for luciferase activity contributes trace amounts of thiol-compounds, e.g. thiols of cellular origin, or from a separate lysis solution to the reaction mixture. In a preferred embodiment, the invention provides a method of detecting luciferase activity in a sample, comprising incubating the sample in the presence of luciferin and ATP and a divalent cation to allow the generation of a light signal, wherein the total light yield of said light signal is enhanced by performing the incubation in a reaction mixture comprising ammonium ions and phosphate ions but no exogenous or supplementary thiol compound (i.e. no thiol-compounds of non-cellular origin), and measuring the light signal. Preferably, the reaction mixture comprises at least 20 mM, more preferably more than 60 mM, like 100, 150, 200, 250, 350, 400, 500 mM or even 1 or 1.5 M phosphate ions, optionally in combination with at least 60 mM or preferably at least more than 100 mM ammonium ions.

Whereas the teaching of the invention makes the inclusion of thiol-compounds unnecessary, it is to be noted that the present invention is not limited to assay conditions without thiol-compounds. DTT, glutathione and/or CoA, or any other commonly used assay component known in the art, can be present in the reaction mixture. However, the use of an odourless, non-thiol reducing agent is preferred. For example, a water-soluble, organic phosphine-containing compound such as Tris (2-carboxyethyl)phosphine hydrochloride (TCEP) may be used (see WO03/044223) in a method of the invention. The present inventors also identified other suitable reducing agents as being suitable for use in luciferin-luciferase reaction mixture, such as thiosulfate, sulfite and dithionite (see Example 3 and FIG. 4). The reducing agent is typically present in an amount of 0.1 to 10 mM.

Apart from the substances mentioned above, the reaction mixture may contain all usual substances which are used in luciferin-luciferase reaction mixtures.

A method of the invention allows the sensitive and convenient detection of luciferase activity in a sample. A sample may comprise cells (suspected of) comprising luciferase activity. A sample can be a suspension, an extract or lysate of cells, for example cells that have been provided with a nucleic acid encoding luciferase. Beyond the availability of crystalline luciferases isolated directly from the light organs of beetles, cDNA's encoding luciferases of several beetle species (including, among others, the luciferase of *P. pyralis* (firefly), the four luciferase isozymes of *P. plagiophthalamus* (click beetle), the luciferase of *L. cruciata* (firefly) and the luciferase of *L. lateralis*) (de Wet et al., Molec. Cell. Biol. 7, 725-737 (1987); Masuda et al., Gene 77, 265-270 (1989); Wood et al., Science 244, 700-702 (1989); EP 0 353 464) are available. Further, the cDNA's encoding luciferases of any other beetle species, which make luciferases, are readily obtainable by the skilled person using known techniques (de Wet et al. Meth. Enzymol. 133, 3-14 (1986); Wood et al., Science 244, 700-702 (1989). Also encompassed is the detection of mutant luciferase activity, for example luciferase that is genetically engineered to improve its properties, such as a non-naturally occurring luciferase with an increased pH stability or increased thermal stability. Other useful mutants are luciferases which include modifications which cause a change in color in the luminescence that is produced. These are for example described in U.S. Pat. No. 6,387,675.

Firefly luciferase can be reliably expressed from various expression vectors and in a diversity of organisms as a reporter in studies of gene regulation. Luciferase reporter assay systems are currently one of the best non-toxic, rapid and sensitive methods to measure gene expression. The assay is based on the detection of luciferase activity which correlates with transcription due to DNA regulatory elements in genes, mutations within those elements as well as responses to extracellular and intracellular signals.

In a preferred embodiment, a method of the invention is applied to quantify the activity of luciferase that is used as reporter enzyme. The basic steps for the use of the luciferase reporter gene system are as follows: 1) construction of an appropriate luciferase reporter vector; 2) transfection of the plasmid DNA into cells to allow luciferase expression; 3) optionally preparation of cell extracts and 4) measurement of luciferase activity evidenced by a light signal. According to the invention, the latter measurement is performed in the presence of both phosphate and ammonium to increase the overall light yield.

As with all reactions, temperature affects the rate of luciferase activity. An accepted range for optimal luciferase assay is between 20-25° C. Ambient room temperature falls within this range and is convenient for performing the assay. Samples and all buffers are therefore preferably allowed to equilibrate to room temperature to obtain consistent and reproducible results. At temperatures above 30° C., the light emission shifts to red and the enzyme quickly degrades.

Under conditions of excess ATP, luciferin and $Mg^{2+}$ relative to the amount of luciferase to be detected, the initial peak height and integrated total light output from a reaction is proportional to the amount of functional luciferase enzyme. The light production optimum however occurs only in rather narrow substrate concentration ranges which exceed the $K_m$ value. At lower ATP concentrations, light emission peak heights are reached and remain at that level for extended periods of time while at higher ATP concentrations the initial light burst is increased but so is the rate of decay. There exist two sources of ATP in luciferase lysate: the known amount which is added to the sample and the unknown and variable amount of endogenous cellular ATP which is co-extracted in the luciferase sample. The absolute final concentration will be somewhat uncertain. For most assay conditions, 0.5-2.5 mM ATP in the assay reaction mixture will be optimal.

The remaining reaction cofactor and substrate components of the system, primarily $Mg^{2+}$ (or $Mn^{2+}$) and luciferin, also have optimal concentrations. They tend to have a wider range of these values than that of ATP. Magnesium ions are preferably present in an amount of at least 0.5 mM. Usually, the concentration of $Mg^{2+}$ in the reaction mixture does not exceed 50 mM. For most conditions, a final luciferin concentration of 0.5-1.0 mM and $Mg^{2+}$ concentrations of 1-5 mM are near optimum. The relatively low concentrations of $Mg^{2+}$ in cell extracts are generally insufficient to alter reaction rates and firefly luciferin is not a natural component found in other organisms. The use of $Mg^{2+}$ and $Ca^{2+}$ free wash buffers for cells is recommended if cell lysates are prepared. Luciferin is preferably present in an amount of between 0.01 and 3 mM, more preferably between 0.05 and 1.0 mM.

When relative experimental luciferase activities are to be correlated to an absolute value, a purified luciferase standard curve can be utilized. Since measured levels of activity are normally stated in RLUs, or relative light units, an absolute value is not being determined. RLU values can vary significantly with the same sample when measured by different instruments due to variations in equipment design and calibration. A specific activity certified luciferase standard, when reconstituted to the manufacturer's specifications, will result in a signal derived from a known luciferase quantity. These known specific activity reference values may be used to normalize arbitrary RLU sample measurements to a given instrument. Additionally, a purified luciferase standard does not necessarily represent the exact amount of luciferase produced by transfected cells, since the specific activity of the expressed luciferase may differ from the purified luciferase.

For the measurement of (heterologously) expressed luciferase activity in a method of the invention, a suspension of cells suspected to contain luciferase can simply be added to a reaction buffer comprising a lysis agent. No separate lysis step is thus required. Upon lysis of the cells, the luciferase becomes accessible to other components of the reaction buffer (substrates, cofactors, ammonium and phosphate ions, and the like) such that the luciferin-luciferase reaction can take place. Typical lysis agents are non-ionic detergents such as Tergitol™ NP-9, Triton™ X-100, Thesit™ and Tween™ 20.

In another embodiment, the sample comprises a cell lysate or cell extract, i.e. the luciferase is first extracted from cells expressing luciferase. There are two main approaches for extraction of luciferase, either through mechanical or chemical methods. Both methods have advantages and disadvantages and evaluation of the method used is important for efficient luciferase extraction and optimal assay sensitivity.

A cell lysate comprises cellular components that are no longer organized into a recognizable intact cellular architecture. Cell lysates may have soluble and insoluble components, either of which may be removed before using the lysate. Lysates may be prepared by any means, including mechanical disruption using sonication, a dounce, mortar and pestle, freeze-thaw cycling, or any other device or process that destroys the physical integrity of cells; or chemical lysis by detergents such as zwitterionic and nonionic detergents, or cationic detergents The most commonly used mechanical lysis method for cell disruption is sonication. Due to large amounts of energy coupled into the sample, heating can develop. Luciferase is heat labile; therefore the sonication method should take this into account by using short sonication cycles. Sample cooling along with five 5-10 second sonication bursts is normally adequate for lysis with minimal luciferase inactivation. Freeze-thaw lysis with multiple cycles is also widely utilized for luciferase assays. The disadvantage of this mechanical lysis method is that luciferase tends to stay bound to the cellular debris pellet after centrifugation. An advantage is the lack of interference from cell disruption chemicals.

Significant improvement and convenience of lysis of eukaryotic cells can be achieved by chemical lysis. Using non-ionic detergents such as 1% Triton™ X-100, greatly enhances solubilization of luciferase from cellular components. Due to better recovery and luciferase activity stimulation by detergent, as much as a 25-fold greater light output is possible over simple freeze-thaw lysis. Other cationic and zwitterionic detergents can be useful for eukaryotic cell lysis and tend to stimulate luciferase activity as well. Anionic detergents, however, generally inhibit luciferase activity. A proper buffering system is also required in optimizing enzyme activity. Lysis reagents with Tris-phosphate, Tricine or phosphate buffers, pH 7.5 to 8.0, are preferred for maximal luciferase stability. The addition of DTT can aid in preserving enzyme function; chelating agents like EDTA or EGTA are preferably included for chelation of e.g. $Mg^{2+}$ and $Ca^{2+}$-ions to suppress the activity of e.g. proteases that might adversely affect the luciferase and chelation of heavy metal ions which may inhibit luciferase activity. Due to the nature of bacterial physiology, the inclusion of detergents alone for bacterial lysis proves inadequate. Additional disruption of the bacterial cell walls generally requires enzymatic and or mechanical lysis steps in order to be successful. The combination of 1% Triton X-100 and 1 mg/ml lysozyme can be used for lysis without affecting luciferase activity or stability. Moderate amounts of luciferase bound to cell debris remain unextractable. A possible alternative is the use of unclarified bacterial lysate without centrifugation, which may increase sensitivity but lower reproducibility because of non-homogeneous distribution of enzyme in the extract.

Another aspect of the invention relates to an assay reagent for the detection of luciferase activity which comprises phosphate and ammonium ions. Said assay reagent may be in a concentrated form which upon dilution into the reaction mixture provides the desired final concentrations of phosphate and ammonium ions. Preferred (concentrated) assay reagents comprise at least 40 mM phosphate, more preferably at least 100 mM phosphate, most preferably at least 250 mM phosphate ions and/or at least 20 mM ammonium ions, preferably at least 100 mM, most preferably at least 250 mM ammonium ions. In a specific aspect, the ammonium ions in the assay reagent are present in excess of phosphate ions, for example 1.1-fold excess, or 1.5-2.0-fold excess or even higher excess. Preferred assay reagents are those containing Tris, ethanolamine and/or ammonium phosphate $(NH_4)_2HPO_4$ neutralized with phosphoric acid to neutral pH. However, other combinations of ammonium and phosphate sources may be used as well. Exemplary assay reagents are those described in the Examples below.

The assay reagent may be in a liquid form (e.g. an aqueous solution) or in a solid form which upon reconstitution provides the phosphate and ammonium ions. Preferred assay reagents comprise as a source of ammonium ions a compound selected from the group consisting of ammonium salts, an amine, a zwitterionic compound, and combinations thereof. Other preferred assay reagents comprise as a source of phosphate phosphoric acid or a salt thereof. An assay reagent may also comprise other useful substances, such as a stabilizer, chelating agent, reducing agent and/or cell lysing agent. In one embodiment, the invention provides an assay reagent comprising all the components necessary for a luciferin-luciferase reaction to occur, except for the luciferase. This type of "all-but-one" assay reagent can simply be contacted with a source of luciferase, e.g. a suspension of cells expressing luciferase, to obtain a light signal. An example of an "all-but-one" assay reagent comprises a Tris-phosphate buffer pH 7, D-luciferin, ATP, $Mg^{2+}$, EDTA, $Ca^{2+}$, thiosulfate and a non-ionic detergent to lyse the cells. A person skilled in the art will be able to prepare many variants of the assay reagent, as long as both ammonium and phosphate ions are present.

In a preferred embodiment, the assay reagent does not comprise DTT because luciferin was found to be more stable in the absence of DTT. The stability of luciferin in the absence of DTT allows to prepare an all-but-one assay reagent with a sufficiently long shelf-life.

Also provided is a kit for use in a luciferase activity assay, for instance a gene reporter assay, wherein said kit comprises components required to perform a luciferase activity assay as provided herein. Such kit components include luciferase substrate (luciferin), cosubstrate (ATP), cofactors such as $Mg^{2+}$ or $Mn^{2+}$, a reducing agent such as sodium thiosulfate and a source of phosphate and ammonium ions.

Preferably, the kit comprises an assay reagent mentioned above. Other useful kit components include a lysis buffer, preferably a non-ionic detergent. Preferably, the kit components are put together in a minimal number of separate containers. Premixing of components reduces the number of handling steps performed by the user of the kit. In one embodiment, the invention provides a luciferase detection kit comprising a first container with a substrate mixture comprising luciferin, ATP and a reducing agent and a second container with a buffer solution comprising at least phosphate and ammonium ions and a bivalent cation. The buffer solution may furthermore comprise further useful substances, such as a stabilizer, chelating agent and/or cell lysing agent Of course, either or both the substrate mixture and the buffer solution may comprise other useful ingredients, such as additional (buffer) salts, chelating agents, cell lysing agent, bivalent cations ($Mg^{2+}$; $Mn^{2+}$), stabilizers and the like. In a preferred embodiment, a kit comprises a lyophilised substrate mixture that can be reconstituted with the buffer solution to yield a ready-to-use detection buffer. The freshly prepared detection buffer can then be added to a sample to be analysed for luciferase activity. Any of the phosphate and ammonium ion sources mentioned above may be used in the buffer solution. In a specific aspect, the invention provides a kit wherein the ammonium ion in buffer solution is provided by Tris or (di)ethanolamine. Said buffer solution is preferably neutralized with $H_3PO_4$.

A kit of the invention may also comprise a cell lysing solution. A kit may furthermore comprise (purified) luciferase enzyme which can be used as a positive control or to prepare a luciferase standard curve.

In a specific aspect, a kit of the invention comprises a freeze-dried substrate mixture and a buffer solution which is to be added to the freeze-dried substrate mixture to yield a ready-to-use luciferase detection reagent. The freeze-dried substrate mixture comprises ATP, luciferin and thiosulfate. The substrate mixture may further comprise other useful components known in the art, such as AMP which further enhances the half-life of the light-signal. The buffer solution comprises ammonium, phosphate, detergent (cell lysing agent), $Mg^{2+}$, EDTA, $Ca^{2+}$ and $(NH_4)_2SO_4$.

The invention is illustrated by the Examples below.

EXAMPLES

Example 1

Figure 1:
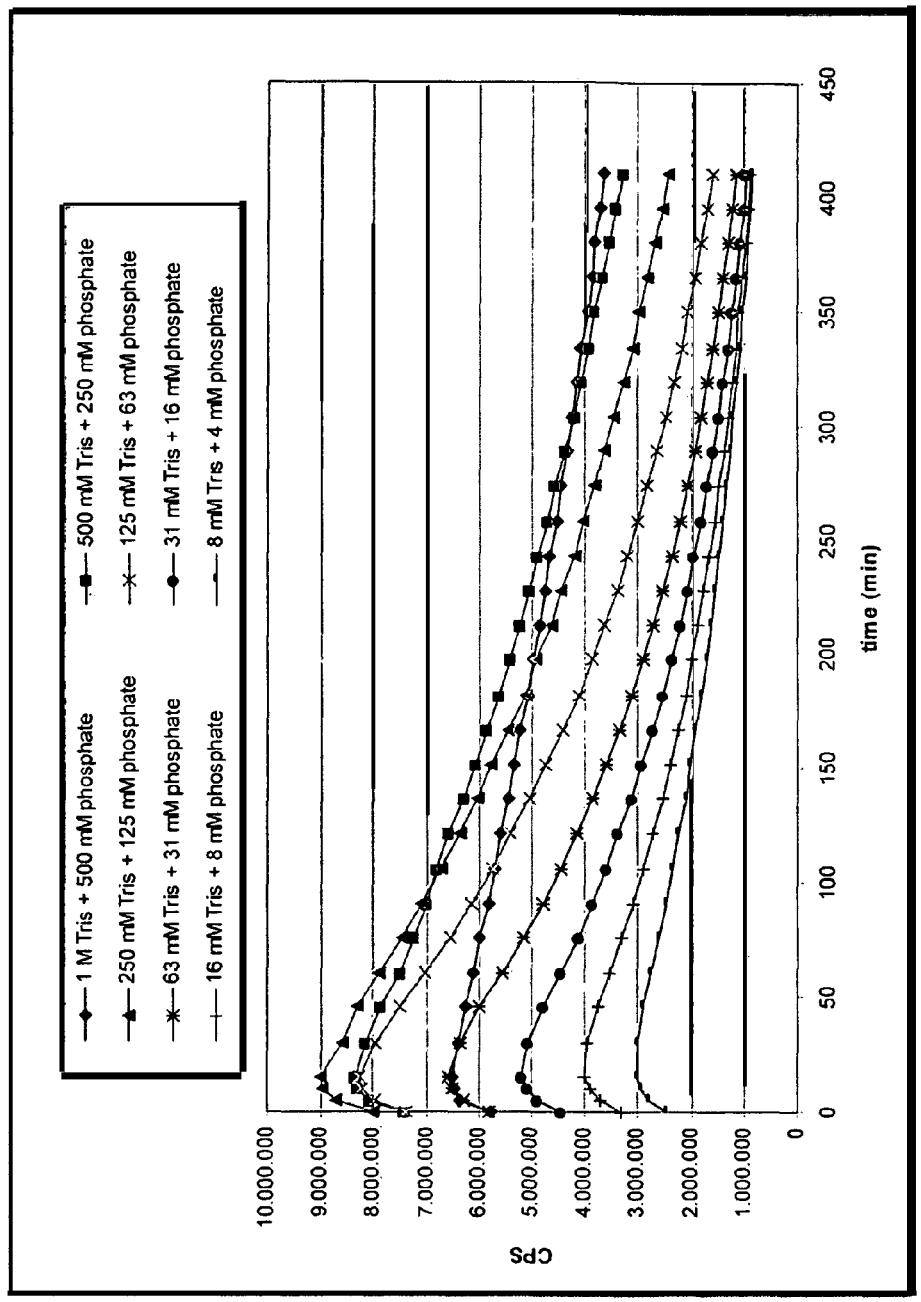
FIG. 1: Light-output time course of the luciferin-luciferase reaction at different concentrations of ammonium ions (Tris) and phosphate ions.

Effect of Different Concentrations of Ammonium and Phosphate Ions

This example demonstrates the effect of different concentrations of Tris and phosphate on the performance of a luciferin-luciferase reaction.

A stock solution of 4.0 M Tris (source of ammonium ions) was neutralized with phosphoric acid ($H_3PO_4$) until a pH of 7.0 was reached. This stock buffer solution contained 2.0 M of phosphate. The stock solution was used to make a range of assay reagents comprising, respectively, 2.2, 1.1, 0.55, 0.275, 0.138, 0.069, 0.034 and 0.017 M Tris. The phosphate concentration in these assay reagents was 1.1, 0.55, 0.275, 0.138, 0.069, 0.034, 0.017 and 0.085 M phosphate, respectively.

Each reagent was checked for its pH to be 7.0 and was adjusted with small amounts of $H_3PO_4$ (several μl of a 2 M $H_3PO_4$ solution) if needed. The phosphate anions added in this manner had no significant effect on the above reported phosphate concentration. Each assay reagent was supplemented with D-luciferin, ATP and sodium-thiosulfate ($Na_2S_2O_3$) by the addition of 250 μl of a freshly prepared stock solution (30 mM ATP, 3 mM D-luciferin, 100 mM thiosulfate adjusted to pH=7.0 with 1 M NaOH) to 2250 μl of assay reagent.

Luciferase was lyophilized in Dulbecco's-PBS with Mg and Ca ($D'PBS^{++}$) containing 0.05 g/ml trehalose and 0.016 g/ml BSA). Luciferase samples were prepared by reconstituting lyophilized luciferase in 200 μl water. The resulting solution was then diluted 100-fold by adding 150 μl of the reconstituted luciferase to 15 ml PBS (8.1 mM $NaH_2PO_4$, 1.5 mM $KH_2PO_4$, 2.7 mM KCl and 137 mM NaCl) containing 5 mM $MgCl_2$, 5 mM $CaCl_2$, 5 mM EDTA, 0.4% Thesit (a non-ionic detergent) and 0.1% bovine serum albumin (BSA). This yielded the "luciferase sample" solution which contained 27 ng/ml of luciferase.

To measure the luminescence kinetics of the luciferin-luciferase reaction for each Tris-phosphate concentration, 100 μl of each assay reagent (Tris-phosphate dilution with D-luciferin, ATP and thiosulfate) was added to a well of a white 96-wells microplate after which 100 μl sample solution was added. The microplate was shaken for 10 seconds at 1100 rpm on a microplate-shaker and then immediately placed in a TopCount®-NXT Microplate Scintillation and Luminescence Counter. The resulting luminescent light signal was measured immediately after loading the microplate into the counter. The measurement was repeated after 5 and 10 minutes. Hereafter the signal was measured repeatedly with 15 minute intervals to a total time of 420 minutes. Between the successive measurements the microplate was kept constantly in the counter at 22° C. The emitted light was quantified as counts per second (cps), count time 3 seconds per well.

Final Tris concentrations in the different reaction mixtures were: 1.0, 0.5, 0.25, 0.125, 0.063, 0.031, 0.016 and 0.008 M. The phosphate concentrations were 0.5, 0.25, 0.125, 0.063, 0.031, 0.016, 0.008 and 0.004 M phosphate ions respectively. Final $Mg^{2+}$, D-luciferin, ATP, thiosulfate and luciferase concentrations in the reaction mixtures were 2.5 mM, 150 μM, 1.5 mM, 5 mM and 14 pg/μl, respectively.

FIG. 1 illustrates the effect of increasing Tris-phosphate concentrations in the luciferin-luciferase reaction mixture on the initial height and the decay of the light signal. To compare the total light yield (expressed as $10^9$ counts) of each reaction mixture the areas under the curves were calculated by integrating the equations of the curves between 0 and 420 minutes. These equations of the curves were obtained using the option 'trend line with equation' of Microsoft Excel® software. The results of these light yield calculations are summarized in Table 3.

FIG. 1 and Table 3 show that increasing the ammonium ions and phosphate ions in luciferase-detection reaction mixture result in both an increase of the initial light signal as well as total light yield up to a final concentration of 0.5 M Tris/0.25 M phosphate. Above these concentrations the initial light signal and, to a smaller extent, the total light yield decreased relative to the values obtained using 0.5 M Tris/0.25 M phosphate, indicating that these concentrations are above the optimal concentrations. As is clear from Table 3, the use of supra-optimal concentrations of ammonium and phosphate ions still result in improved light yield when compared to low or very low ammonium/phosphate concentrations. Therefore, a method of the invention is not limited to the use of suboptimal or optimal ion concentrations.

TABLE 3

Light yield of the luciferin-luciferase reaction as function of Tris and phosphate concentration from FIG. 1

| [Tris] (M) | [Phosphate] (M) | Light Yield ($10^9$ counts) |
| --- | --- | --- |
| 1.0 | 0.5 | 123.8 |
| 0.5 | 0.25 | 137.3 |
| 0.25 | 0.125 | 126.8 |
| 0.125 | 0.063 | 103.4 |

TABLE 3-continued

Light yield of the luciferin-luciferase reaction as function of Tris and phosphate concentration from FIG. 1

| [Tris] (M) | [Phosphate] (M) | Light Yield ($10^9$ counts) |
|---|---|---|
| 0.063 | 0.031 | 80.4 |
| 0.031 | 0.016 | 63.0 |
| 0.016 | 0.008 | 52.9 |
| 0.008 | 0.004 | 44.4 |

Example 2

Effect of Different Sources of Ammonium Ions

This example demonstrates the advantageous effects on light yield if ethanolamine or ammonium phosphate is used to provide the luciferin-luciferase reaction with ammonium ions.

Stock solutions of 4.0 M ethanolamine ($H_2NCH_2CH_2OH$) and 3.0 M ammonium-phosphate (($NH_4$)$_2HPO_4$) were neutralized with phosphoric acid ($H_3PO_4$) until pH 7.0 was reached. Dilutions were made in the same manner as described in example 1. Furthermore, all methods and other chemicals used to create the assay mixture and to test this for its light yield in a luciferin-luciferase reaction, were standardized and thus the same as in example 1. Final ethanolamine concentrations in the assay were 1.0, 0.5, 0.25, 0.125, 0.063, 0.031, 0.016 and 0.008 M, and 0.5, 0.25, 0.125, 0.063, 0.031, 0.016, 0.008 and 0.004 M phosphate, respectively. According to the present invention, a final concentration of 1M ethanolamine is assumed to provide the aqueous, neutral reaction mixture with 1M of ammonium ions. Thus, the concentration of ammonium ions in the reaction mixture is regarded to be identical to that of the source of ammonium ions.

In the case of ($NH_4$)$_2HPO_4$, the ammonium salt provides both the ammonium and phosphate ions. In the dilutions tested, the ammonium ($NH_4^+$) concentrations in the final mixture were 2.0, 1.0, 0.5, 0.25, 0.125, 0.063, 0.031 and 0.016 M and these dilutions contained respectively 1.4, 0.70, 0.35, 0.17, 0.085, 0.043, 0.021 and 0.011 M phosphate in the final reaction mixture. Each tested ammonium-phosphate dilution also contained a small amount of 28 mM MOPS (3-(N-morpholino)propanesulfonic acid).

FIG. 2 shows the results of measuring the light signal in a luciferin-luciferase reaction mixture comprising different amounts of ethanolamine-phosphate (panel A) or ammonium-phosphate (panel B). Quantification of the reaction kinetics through surface area calculation under the curves is shown in Table 4 (ethanolamine-phosphate dilutions) and Table 5 (for ammonium-phosphate dilutions).

As with Tris-phosphate, incrementing the ethanolamine-phosphate concentration gives rise to a better light yield, but only up to 0.5 M ethanolamine with 0.25 M phosphate. At 1.0 M ethanolamine with 0.5 M phosphate the reaction results in a reduced light yield when compared to the reaction mixture with 0.5 M ethanolamine with 0.25 M phosphate. Apparently, these concentrations are above optimum but nevertheless useful. Increasing ammonium-phosphate combinations up to 500 mM ammonium and 350 mM of phosphate also causes increased light yield. At higher concentrations the light yield decreases.

TABLE 4

Figure 2A:
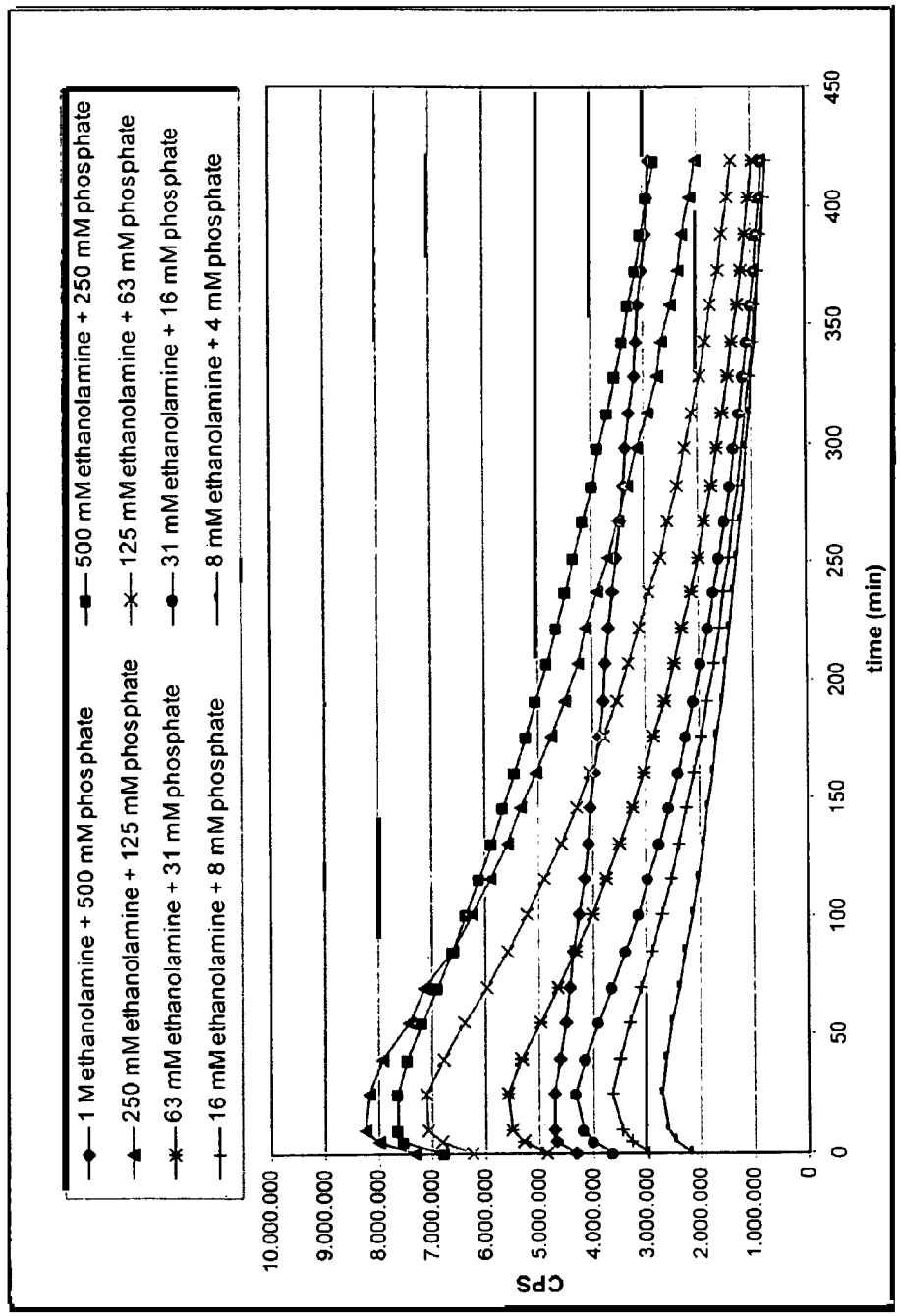
FIG. 2A-B: Light-output time course of the luciferin-luciferase reaction at different concentrations of ethanolamine and phosphate (panel A) or ammonium and phosphate (panel B).

Light yield of the luciferin-luciferase reaction as function of ethanolamine and phosphate concentration from FIG. 2A

| [Ethanolamine] (M) | [Phosphate] (M) | Light Yield ($10^9$ counts) |
|---|---|---|
| 1.0 | 0.5 | 99.0 |
| 0.5 | 0.25 | 124.8 |
| 0.25 | 0.125 | 115.4 |
| 0.125 | 0.063 | 96.2 |
| 0.063 | 0.031 | 70.0 |
| 0.031 | 0.016 | 59.2 |
| 0.016 | 0.008 | 49.6 |
| 0.008 | 0.004 | 41.6 |

TABLE 5

Figure 2B:
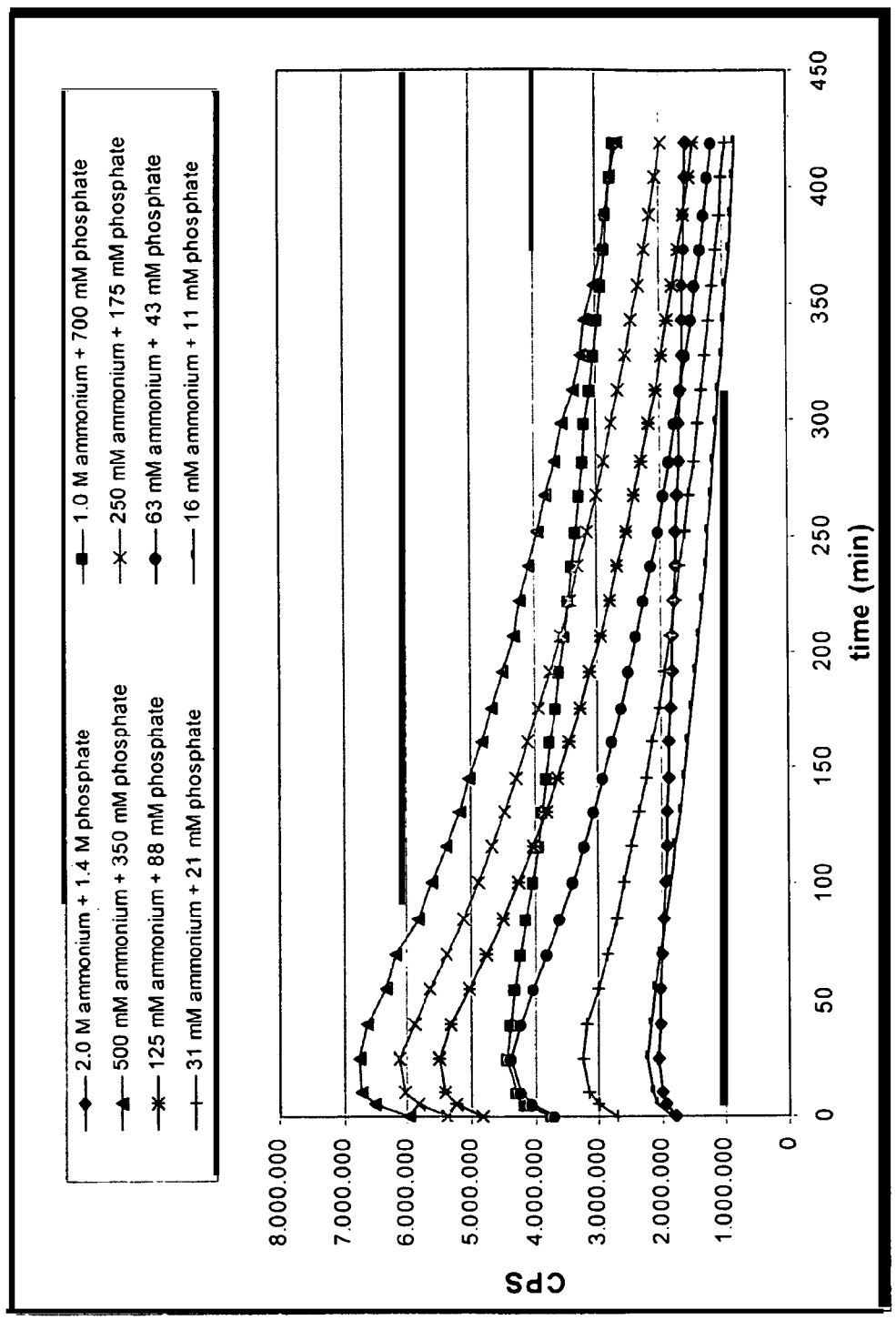

Light yield of the luciferin-luciferase reaction as function of ammonium and phosphate concentration from FIG. 2B

| [Ammonium] (M) | [Phosphate] (M) | Light Yield ($10^9$ counts) |
|---|---|---|
| 2.0 | 1.4 | 44.6 |
| 1.0 | 0.7 | 80.7 |
| 0.5 | 0.35 | 113.1 |
| 0.25 | 0.175 | 88.9 |
| 0.125 | 0.088 | 83.2 |
| 0.063 | 0.043 | 69.3 |
| 0.031 | 0.021 | 43.7 |
| 0.016 | 0.011 | 31.8 |

Example 3

Effect of Different Types of Reducing Agents

This example demonstrates the effect of various types of reducing agents used to protect the reactive sulfhydryl group of luciferase from oxidation. This can be important for a sustained activity of the enzyme. (DeLuca et al. Biochemistry 3:935 (1964); and Lee et al., Biochemistry 8:130-136 (1969)). Various protective agents were compared against a control sample not containing a reducing agent in a luciferin-luciferase reaction comprising ammonium and phosphate ions (0.5 M Tris and 0.25 M phosphate).

Stock solutions containing 100 mM of the following reducing agents were prepared: sodium-dithionite ($Na_2S_2O_4$), dithiothreitol (DTT), Tris(2-carboxyethyl) phosphine (TCEP), sodium-thiosulfate ($Na_2S_2O_3$) and sodium-sulfite ($Na_2SO_3$). The TCEP stock solution was prepared by dissolving the hydrochloride salt (TCEP.HCl).

A 3.5 M Tris/1.8 M phosphate stock solution was diluted to a concentration of 1.2 M Tris/0.62 M phosphate (or 1.11 M/0.56 M for $Na_2S_2O_4$). For each reducing agent a detection buffer was made by diluting 100 µl of each reducing agent's stock (10 µl for $Na_2S_2O_4$) in 800 µl Tris-phosphate buffer solution (890 µl for $Na_2S_2O_4$). The detection buffer was completed by adding 100 µl of a freshly made solution with 30 mM ATP, 3 mM D-luciferin, pH 7.0. Luciferase samples and light signal measurements were performed as described above. The final concentration of the reducing agent in the reaction mixture was 5 mM for DTT, TCEP, $Na_2S_2O_3$ and $Na_2SO_3$ and 0.5 mM for $Na_2S_2O_4$.

The time course of the light signal (FIG. 3) and the resulting light yield of each reaction (Table 6) show that the presence of a reducing agent in the reaction mixture to protect the luciferase from oxidation results in a large increase in light yield. Furthermore, the results demonstrate the suitability of dithionite, thiosulfate, sulfite and TCEP as non-thiol reducing agents in a luciferin-luciferase assay.

TABLE 6

Figure 3:
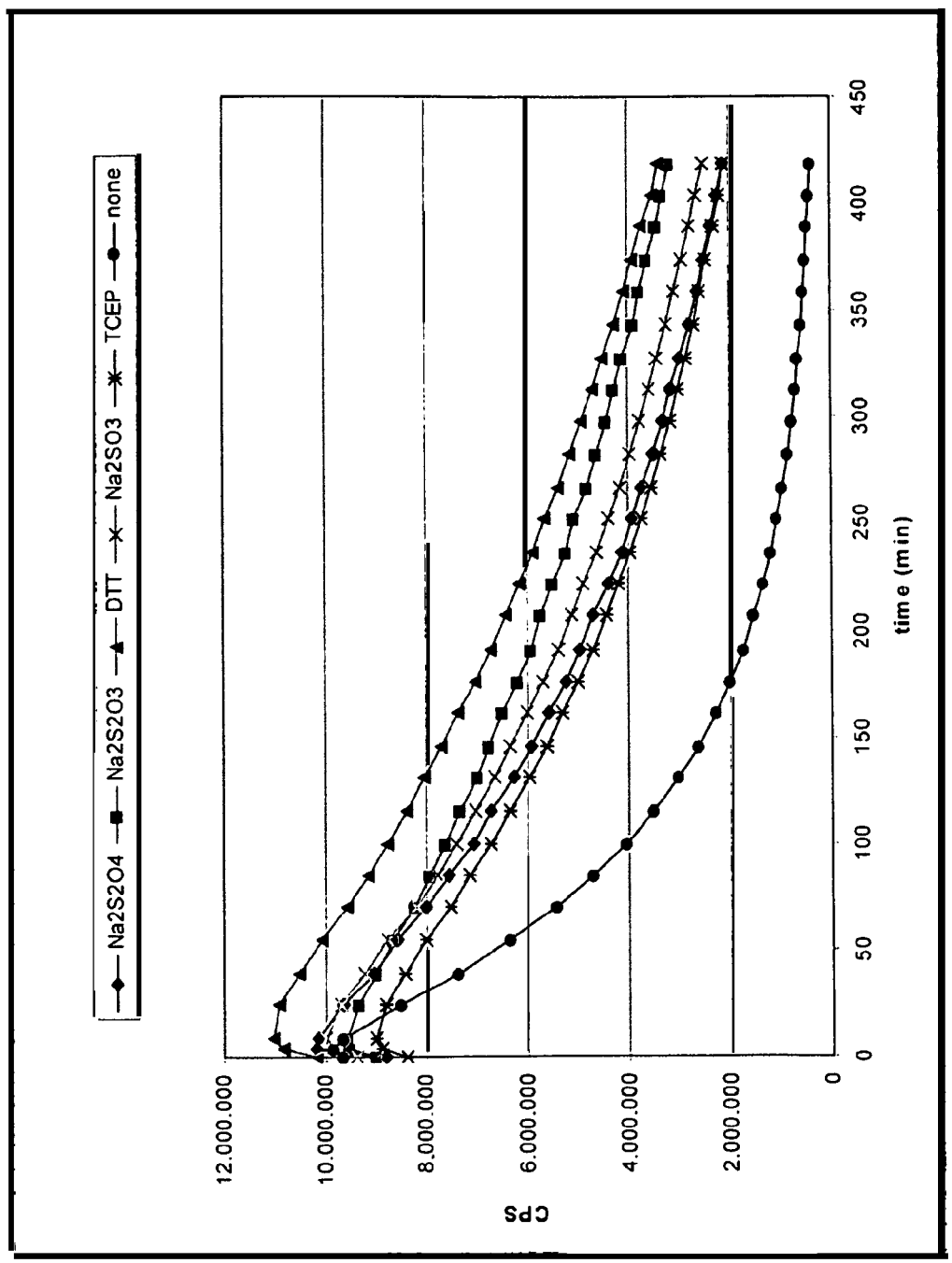
FIG. 3: Light-output time course of the luciferin-luciferase reaction comprising Tris (0.5 M), phosphate (0.25 M) and various reducing agents.

Light yield of the luciferin-luciferase reaction as function of various reducing agents from FIG. 3

| Reducing Agent | Light Yield ($10^9$ counts) |
|---|---|
| $Na_2S_2O_4$ | 128.4 |
| $Na_2S_2O_3$ | 147.7 |
| DTT | 167.5 |
| $Na_2SO_3$ | 136.8 |
| TCEP | 122.1 |
| none | 65.9 |

Example 4

Differential Effect of Different Ammonium/Phosphate Ion Concentrations on the Luciferin-Luciferase Reaction in an ATP-Detection Versus a Luciferase-Detection Assay This example demonstrates that increasing the amounts of ammonium ions and phosphate ions in the luciferin-luciferase reaction mixture has a different effect on an ATP-detection system than on a luciferase-detection system.

For this experiment 16 different reagent mixtures were prepared; 8 mixtures (for the ATP assay) contained a large amount of luciferase, a small amount of ATP and increasing Tris-phosphate concentrations and 8 mixtures (for the luciferase assay) contained a large amount of ATP, a small amount of luciferase and increasing amounts of Tris-phosphate. Final reaction mixture concentrations of each component are shown in Table 7. To reduce variances that might be introduced by small concentrations differences between the reagents, all reagents were made from the same stock solutions where possible.

A "luciferase sample" was prepared by reconstituting a lyophilized luciferase control sample (PerkinElmer Inc.) in $H_2O$ and diluting this in Dulbecco's PBS with Ca/Mg (D'PBS$^{++}$) to a $1.0 \times 10^{-7}$ g/l luciferase solution.

An "ATP sample" was prepared by diluting a reconstituted lyophilized ATP standard (PerkinElmer Inc.) in D'PBS$^{++}$ resulting in a $1.0 \times 10^{-8}$ mM ATP solution.

To measure the luminescence kinetics of the luciferin-luciferase reaction when assaying for ATP, 100 μl of each Tris-phosphate concentration reagent with luciferase was pipetted into a 96-wells CulturPlate™ (PerkinElmer Inc.) and 100 μl of "ATP sample" was added. Likewise, in the same microplate the reaction kinetics when assaying for luciferase were measured by pipetting 100 μl of each Tris-phosphate concentration reagent with ATP, and adding 100 μl of "luciferase sample".

The microplate was shaken for 10 seconds on a microplate-shaker and sealed with TopSeal-A™ (PerkinElmer Inc.). Thereafter the plate was immediately placed in a TopCount®-NTX to measure the emitted light. The luminescent light signal was immediately measured, meaning about 1 minute after mixing reagent and sample, and after 5 and 10 minutes. Hereafter the signal was measured repeatedly with 15 minute intervals to a total time of 420 minutes. Between the successive measurements the microplate was kept constantly in the counter at 22° C. The emitted light was quantified as counts per second (cps), count time 3 seconds per well.

Figure 4A:
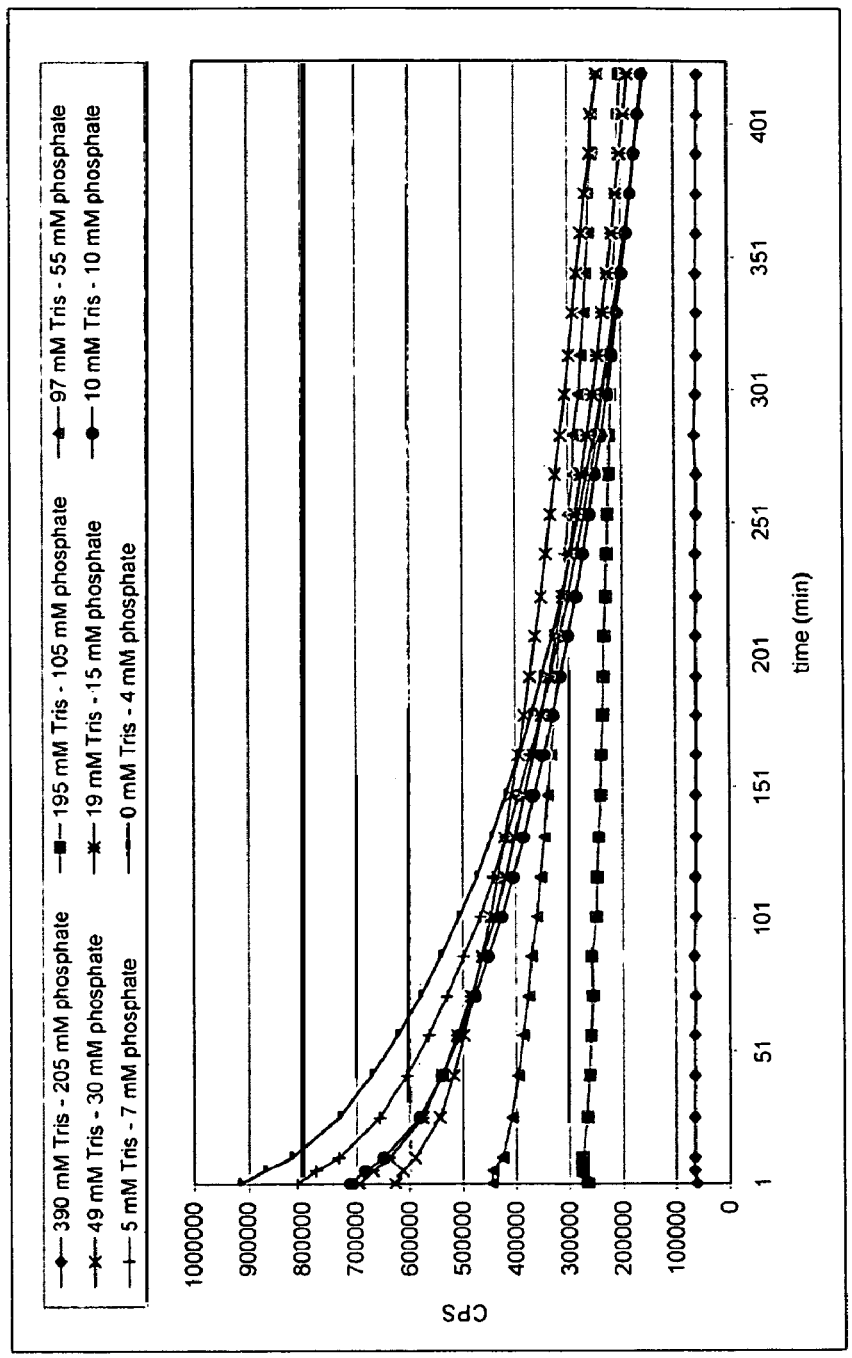
FIG. 4A-B: Effect of different Tris-phosphate concentrations in the reaction mixture on reaction kinetics of a luminescence reaction in (panel A) an ATP-detection system with small amounts of ATP (5 nM) and larger quantities of luciferase (5 mg/l≈8, $3\times10^{-8}$ M) or (Panel B) a luciferase-detection system with small amounts of luciferase ($5.0\times10^{-5}$ mg/l≈8, $3\times10^{-13}$ M) and excess (1.5 mM) ATP.
Figure 4B:
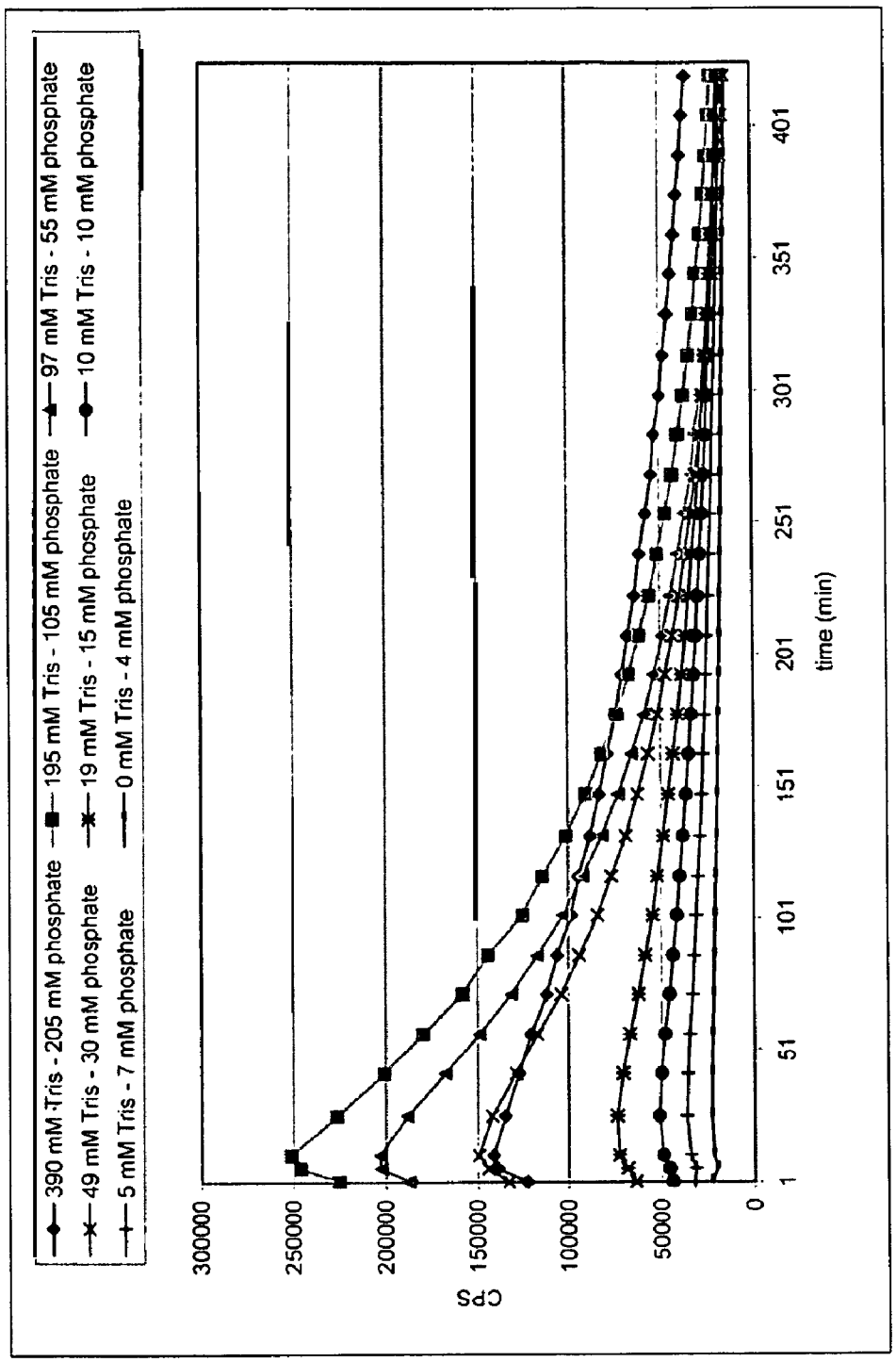

FIG. 4A illustrates the effect of increasing Tris-phosphate concentrations on the reaction kinetics in the ATP detection setting, and FIG. 4B shows the effect for the luciferase detection.

Figure 5:
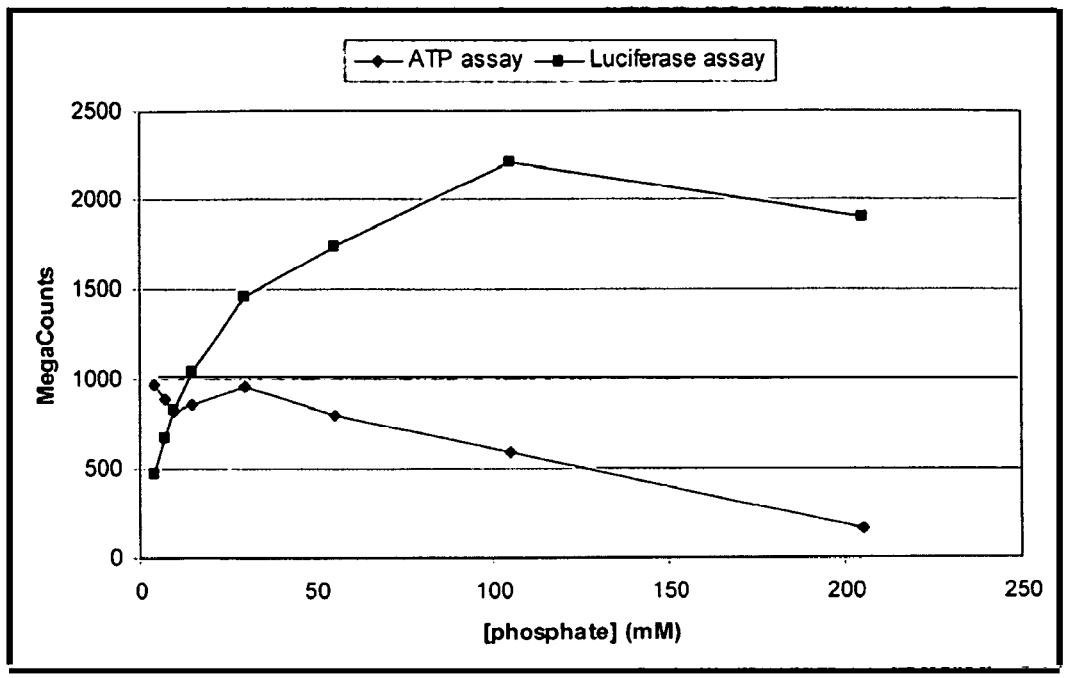
FIG. 5: Total light yield of each luminescence reaction of the ATP and luciferase assay systems of FIGS. 4A en 4B. The integral of each reaction kinetics curve with different Tris-phosphate ion concentration was determined between 1 and 420 minutes. The resulting total luminescence is expressed in MegaCounts ($10^6$ counts) as a function of phosphate ion concentration.

To further illustrate the difference between the ATP and the luciferase detection systems, the total luminescence of each curve, i.e. the integral under that curve between 1 and 420 minutes and expressed in 106 counts, was calculated and plotted in FIG. 5 as a function of the phosphate concentration.

Figure 6:
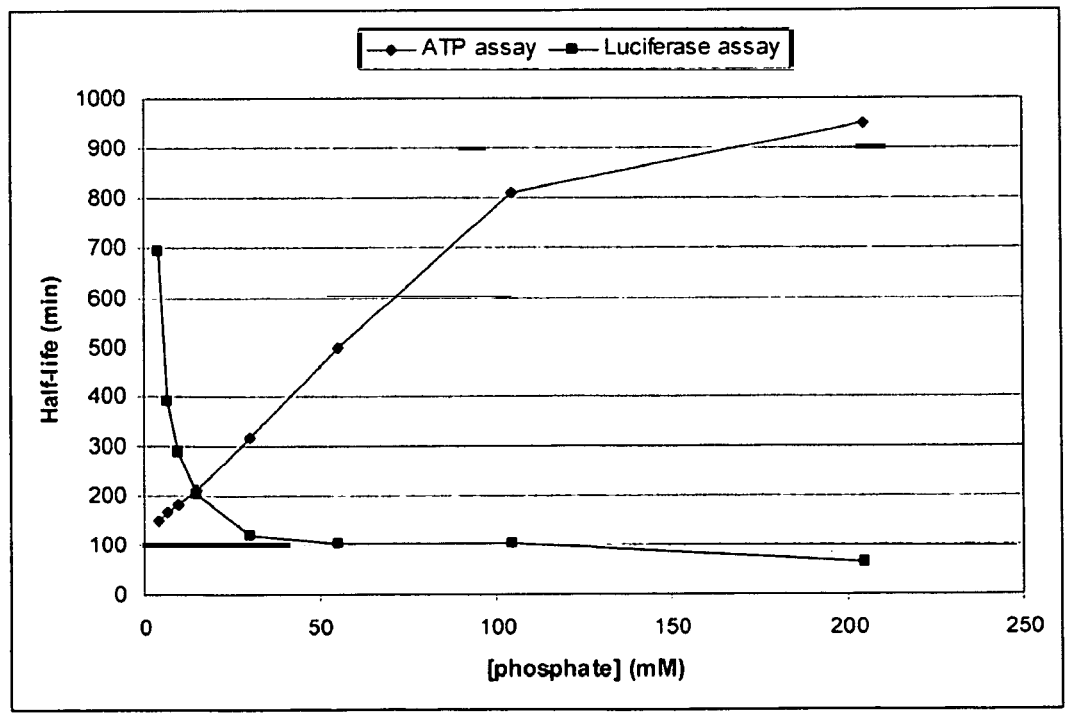
FIG. 6: Effect of phosphate concentration on the half-life (calculated after 10 minutes of incubation) of the luminescence reaction of the ATP and luciferase assay systems of FIGS. 4A en 4B. The half-life is the time needed for the luminescence to decay to half of its initial value.

FIG. 6 shows the relationship between phosphate concentration and the half-life of the luminescence, i.e. the time needed for the luminescence to decay to half its initial value (in minutes), for an ATP and a luciferase assay. Initial luminescence was assessed after 10 minutes of incubation.

The ATP- and luciferase-detection assays clearly perform differently with respect to the increasing ammonium/phosphate ions in the reaction mixture. In an ATP assay, wherein the ratio luciferase-ATP is shifted towards the enzyme, higher Tris-phosphate ion concentrations inhibit total luminescence. Whereas in a luciferase assay, wherein the luciferase-ATP ratio is shifted towards ATP, the presence of up to 100 mM Tris-phosphate enhances total luminescence.

TABLE 7

Concentration of each component in 200 μl reaction mixture per well for the ATP- or luciferase-detection assay.

Concentration of components in final reaction mixture

| Chemical | ATP assay (8 different reaction mixtures) Concentration | | | | | | | | Luciferase assay (8 different reaction mixtures) Concentration | | | | | | | |
|---|---|---|---|---|---|---|---|---|---|---|---|---|---|---|---|---|
| Trehalose | 2.5 g/l | | | | | | | | 2.5 g/l | | | | | | | |
| HEPES | 5 mM | | | | | | | | 5 mM | | | | | | | |
| BSA | 0.5 g/l | | | | | | | | 0.5 g/l | | | | | | | |
| $Na_2S_2O_3$ | 1.5 mM | | | | | | | | 1.5 mM | | | | | | | |
| Tris | 390 | 195 | 97 | 49 | 19 | 10 | 5 | 0 mM | 390 | 195 | 97 | 49 | 19 | 10 | 5 | 0 mM |
| $PO_4^{3-}$ | 205 | 105 | 55 | 30 | 15 | 10 | 7 | 4 mM* | 205 | 105 | 55 | 30 | 15 | 10 | 7 | 4 mM* |
| NaCl | 69 mM | | | | | | | | 69 mM | | | | | | | |
| $CaCl_2$ | 0.45 mM | | | | | | | | 0.45 mM | | | | | | | |
| $MgCl_2$ | 0.25 mM | | | | | | | | 0.25 mM | | | | | | | |
| KCl | 1.3 mM | | | | | | | | 1.3 mM | | | | | | | |
| D-luciferin | 0.5 mM | | | | | | | | 0.5 mM | | | | | | | |

TABLE 7-continued

Concentration of each component in 200 µl reaction mixture per well
for the ATP- or luciferase-detection assay.
Concentration of components in final reaction mixture

| Chemical | ATP assay (8 different reaction mixtures) Concentration | Luciferase assay (8 different reaction mixtures) Concentration |
|---|---|---|
| ATP | $5.0 \times 10^{-9}$ M | $1.5 \times 10^{-3}$ M |
| Luciferase | 5.0 mg/l | $5.0 \times 10^{-5}$ mg/l |
| | pH 7.0 | pH 7.0 |

*Corrected for phosphate ions present in PBS++ used for sample preparation

The invention claimed is:

1. A kit for detecting luciferase activity, comprising an assay reagent and a luciferase substrate, wherein said assay reagent comprises at least 100 mM phosphate ions and more than 200 mM ammonium ions.

2. The kit according to claim 1, wherein said assay reagent comprises at least 200 mM phosphate ions and/or at least 300 mM ammonium ions.

3. The kit according to claim 1, wherein the phosphate ions in the assay reagent are provided by $H_3PO_4$, $H_2PO_4^-$, or $HPO_4^{2-}$, $PO_4^{3-}$ or a combination thereof.

4. The kit according to claim 1, wherein the ammonium ions in the assay reagent are provided by an ammonium salt, an amine or a zwitterionic compound, or a combination thereof.

5. The kit according to claim 4, wherein the ammonium ions are provided by an amine-based buffer, preferably Tris (tris(hydroxymethyl)aminomethane) or Bis-Tris (bis(2-hydroxyethyl)imino-tris(hydroxymethyl)methane).

6. The kit according to claim 4, wherein said amine is a primary or secondary amine, preferably an amine selected from the group consisting of monoethanolamine, diethanolamine, monoethylamine and diethylamine.

7. The kit according to claim 1, wherein ammonium ions in the assay reagent are present in excess of the phosphate ions.

8. The kit according to claim 7, wherein ammonium ions are present in at least 1.4-fold excess of the phosphate ions.

9. The kit according to claim 1, wherein the assay reagent comprises Tris, ethanolamine and/or ammonium phosphate neutralized with phosphoric acid to neutral pH.

10. The kit according to claim 1, wherein the assay reagent comprises Tris-phosphate buffer pH 7, D-luciferin, ATP, $Mg^{2+}$, EDTA, $Ca^{2+}$, thiosulfate and a non-ionic detergent.

11. The kit according to claim 1, wherein the assay reagent comprises no exogenous or supplementary thiol compound.

12. The kit according to claim 1, wherein said luciferase substrate is in a lyophilised form.

13. The kit according to claim 1, further comprising a cell lysing agent.

14. The kit according to claim 13, wherein said cell lysing agent is present in said assay reagent.

15. The kit according to claim 1, further comprising a luciferase standard.

16. The kit according to claim 1, further comprising a non-thiol reducing agent.

17. The kit according to claim 16, wherein the reducing agent is thiosulfate, sulfite, or dithionite.

18. A Luciferase detection reagent comprising at least 100 mM phosphate ions and at least 200 mM ammonium ions, luciferase substrate, ATP, divalent cation and a reducing agent.

19. The reagent according to claim 18, comprising at least 200 mM phosphate ions, and/or at least 300 mM ammonium ions.

20. The reagent according to claim 18, comprising no exogenous or supplementary thiol compound.

21. The reagent according to claim 18, further comprising a stabilizer, chelating agent, reducing agent and/or a cell lysing agent.

22. The reagent according to claim 18, comprising a Tris-phosphate buffer, D-luciferin, ATP, $Mg^{2+}$, EDTA, $Ca^{2+}$, thiosulfate and a non-ionic detergent.

* * * * *